(12) United States Patent
Burroughes et al.

(10) Patent No.: US 7,534,503 B2
(45) Date of Patent: May 19, 2009

(54) MONOMER FOR USE IN PREPARATION OF A POLYMER TO BE USED IN OPTICAL DEVICES

(75) Inventors: Jeremy Burroughes, Cambridge (GB); Carl Towns, Stansted (GB); Thomas Pounds, Cambridge (GB); Jonathan Halls, Cambridge (GB)

(73) Assignee: Cambridge Display Technology Limited, Cambridgeshire (GB)

( * ) Notice: Subject to any disclaimer, the term of this patent is extended or adjusted under 35 U.S.C. 154(b) by 726 days.

(21) Appl. No.: 10/470,049

(22) PCT Filed: Jan. 23, 2002

(86) PCT No.: PCT/GB02/00294

§ 371 (c)(1),
(2), (4) Date: Nov. 10, 2003

(87) PCT Pub. No.: WO02/059121

PCT Pub. Date: Aug. 1, 2002

(65) Prior Publication Data

US 2004/0115473 A1     Jun. 17, 2004

Related U.S. Application Data

(60) Provisional application No. 60/310,588, filed on Aug. 7, 2001.

(30) Foreign Application Priority Data

Jan. 24, 2001 (GB) .................................. 0101824.1
Jun. 14, 2001 (GB) .................................. 0114538.2

(51) Int. Cl.
*H01L 51/00* (2006.01)
*C09K 11/02* (2006.01)
*C08G 79/08* (2006.01)

(52) U.S. Cl. ....................... 428/690; 428/917; 313/504; 257/40; 528/7; 528/394; 528/423; 252/301.35

(58) Field of Classification Search ................ 428/690, 428/917; 313/504, 506; 257/40; 252/301.35; 544/349; 549/350; 528/377, 7, 394, 423
See application file for complete search history.

(56) References Cited

U.S. PATENT DOCUMENTS 5,777,070 A   7/1998   Inbasekaran et al. ........ 528/394

(Continued)

FOREIGN PATENT DOCUMENTS

EP     544 795 B2     6/1993

(Continued)

OTHER PUBLICATIONS

Mullekom et al., Band-Gap Engineering of Donor-Acceptor-Substituted pi-Conjugated Polymers, Chem. Euro. J. 1998, 4, No. 7, 1235-1243.*

(Continued)

*Primary Examiner*—D. Lawrence Tarazano
*Assistant Examiner*—Camie S Thompson
(74) *Attorney, Agent, or Firm*—Marshall, Gerstein & Borun LLP

(57) ABSTRACT

A monomer having general Formula (I) which may be substituted or unsubstituted: where E and E are the same or different and are reactive groups capable of undergoing chain extension; X is O, S, $NR_5$, $R_5C-CR_6$ or $R_5=CR_6$; Y is O, S, $NR_7$, $R_7C-CR_8$ or $R_7C=CR_8$; $R_5$, $R_6$ $R_7$ and $R_8$ are the same or different and each is independently H or a substituent group; and each Ar is the same or different and is independently a substituted or unsubstituted aryl or heteroaryl group.

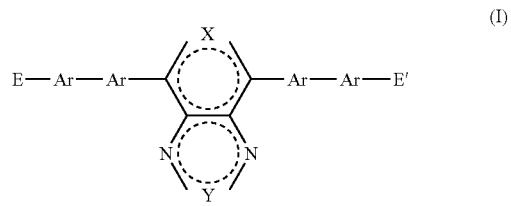

(I)

38 Claims, 3 Drawing Sheets

U.S. PATENT DOCUMENTS

| | | | |
|---|---|---|---|
| 6,242,561 B1 * | 6/2001 | Mohwald et al. | 528/377 |
| 6,309,763 B1 * | 10/2001 | Woo et al. | 428/690 |
| 2005/0064231 A1 * | 3/2005 | Towns et al. | 428/690 |

FOREIGN PATENT DOCUMENTS

| | | |
|---|---|---|
| WO | WO 90/13148 | 11/1990 |
| WO | WO 99/48160 | 9/1999 |
| WO | WO 00/46321 | 8/2000 |
| WO | WO 00/53656 | 9/2000 |
| WO | WO 00/55927 | 9/2000 |
| WO | WO 01/49768 A2 | 7/2001 |
| WO | WO 01/49768 A3 | 7/2001 |
| WO | WO 01/62869 A1 | 8/2001 |

OTHER PUBLICATIONS

International Search Report in PCT/GB02/00294 dated Apr. 5, 2002.
International Preliminary Examination Report in PCT/GB02/00294 dated Apr. 22, 2003.

* cited by examiner

MONOMER FOR USE IN PREPARATION OF A POLYMER TO BE USED IN OPTICAL DEVICES

This is the U.S. national phase of International Application No. PCT/GB02/00294 filed Jan. 23, 2002, and claims the benefit of the filing date of U.S. Provisional Application Ser. No. 60/310,588 filed Aug. 7, 2001, the entire respective disclosures of which are incorporated herein by reference.

The present invention relates to a novel compound, specifically a novel monomer for use in the preparation of a polymer.

A polymer prepared from a monomer according to the present invention is envisaged to be useful in an optical device such as an optical device comprising an electroluminescent device or a photovoltaic device.

Electroluminescent devices are structures which emit light when subjected to an applied electric field. In its simplest form an electroluminescent device comprises a light-emissive layer between two electrodes. The cathode electrode injects negative charge carriers (electrons) and the anode electrode injects positive charge carriers (holes) into the light-emissive layer. Light emission occurs when the electrons and holes combine in the light-emissive layer to generate photons. As a practical aspect, one of the electrodes is typically transparent, to allow the photons to escape the device. The light-emissive layer should be made from a light-emissive material which may be laid down as a film without substantially affecting the luminescent characteristics of the material and which is stable at the operational temperature of the device.

The colour of the light generated by the light-emissive material is determined by the optical gap or semiconductor bandgap of the light-emissive material. The semiconductor bandgap of the light-emissive material is the difference in energy between the "highest occupied molecular orbital" (HOMO) and the "lowest unoccupied molecular orbital." (LUMO) levels. Effectively, the semiconductor bandgap is the energy difference between the valance and conduction bands of the light-emissive material. These levels can be estimated by photoemission measurements and measurements of the electrochemical potentials for oxidation and reduction of the light-emissive material. However, the levels of these energies are affected by numerous factors. Accordingly, the use of such values is indicative rather than quantitative PCT/WO90/13148 discloses an electroluminescent device comprising a semiconductor layer comprising a polymer film as the light-emissive layer which comprises at least one conjugated polymer. In this case, the polymer film comprises a poly(para-phenylene vinylene) (PPV) film.

EP 0544795 discloses the use of a semiconductive conjugated copolymer as the light-emissive layer in an electroluminescent device. The semiconductive conjugated copolymer comprises at least two chemically different monomer units which, when existing in their individual homopolymer forms, typically have different semiconductor bandgaps. The proportion of the chemically different monomer units in the copolymer can be selected to control the semiconductor bandgap of the copolymer so as to control the optical properties of the copolymer. To some degree, the extent of conjugation of the copolymer can be said to affect the bandgap of the copolymer. Increasing the extent of conjugation has the effect of decreasing the bandgap up to the point of bandgap convergence. Therefore, selection of an appropriate polymer structure is one way of selecting the bandgap. This gives the very desirable feature of controlling the colour of the light output from the polymer when made to emit light. This property is useful particularly in the construction of the electroluminescent devices.

Polymers are known that are capable of emitting 'red light' when used in an electroluminescent device. For example, embodiment one described in PCT/GB00/00911 relates to "red light emission". It is further stated that light having a wavelength in the range 600 nm to 700 nm is obtainable with polymers according to embodiment one. WO 00/46321 is concerned with fluorene copolymers and electronic devices (such as polymer light-emitting diodes) containing one or more films derived from the copolymers. It is stated in Table 4 that copolymer 19 can be used in an LED that emits red light. A bandgap of 2.10 electron volts is given in Table 2 for copolymer 19.

It can be seen that there exists a deficiency in the prior art of semiconductive polymers capable of "deep red" emission i.e. red light having a longer wavelength, above 700 nm and towards the IR end of the spectrum when used in an electroluminescent device. It will be understood from the above that the wavelength of emission from a semiconductive polymer when used in an electroluminescent device will be influenced by its structure. Furthermore, it will be understood from the above that the solubility of a semiconductive polymer will be limited by its structure. The structure of a polymer is derived from the monomers from which it is made. Thus, a deficiency exists in the prior art of monomers that are suitable for making a polymer that is capable of "deep red" emission or capable of other wavelengths of emission, particularly "red" emission.

It is an aim of the present invention to overcome at least partially the deficiencies of the prior art and to provide such polymers particularly for use in an optical device. To be used in an optical device, such polymers also desirably have good optical device characteristics. These characteristics include the internal quantum efficiency (number of photons generated relative to the number of charge carriers injected into the polymer), the solubility and processability of the material and the lifetime when used in a device. Also relevant for consideration is the stability of the polymer during use and storage of the device.

As a result of extensive research into polymer structure, the present inventors have found that such a polymer may be prepared from a monomer having general formula I which may be substituted or unsubstituted:

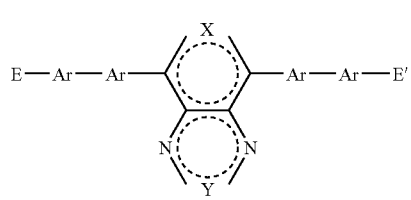

I where E and E' are the same or different and are reactive groups capable of undergoing chain extension; X is O, S, $NR_5$, $R_5C$—$CR_6$ or $R_5C$=$CR_6$; Y is O, S, $NR_7$, $R_7C$—$CR_8$ or $R_7C$=$CR_8$; $R_5$, $R_6$, $R_7$ and $R_8$ are the same or different and each is independently H or a substituent group; and each Ar is the same or different and is independently a substituted or unsubstituted aryl or heteroaryl group.

Accordingly, a first aspect of the present invention provides a monomer having general formula I:

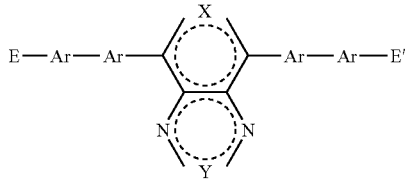

where E and E'; X; Y; $R_5$, $R_6$, $R_7$ and $R_8$ and each Ar are as defined above.

A second aspect of the present invention provides a polymer prepared from a monomer according to the first aspect.

A third aspect of the present invention provides a polymer comprising a first repeat unit comprising a unit having general formula V that is substituted or unsubstituted:

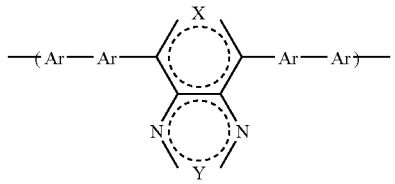

where X, Y and Ar are as shown or defined in the first aspect, provided that none of the Ar groups comprise a mono fluorene group.

A fourth aspect of the present invention provides the use of a polymer according to the second or third aspect in an optical device.

A fifth aspect of the present invention provides the use of a repeat unit having general formula V that is substituted or unsubstituted for accepting and combining positive and negative charge carriers to generate light in a part of a polymer, where X, Y and Ar are as shown or defined in the first aspect of the present invention.

A sixth aspect of the present invention provides a method for making a polymer according to the second aspect.

A seventh aspect of the present invention provides an optical device comprising a polymer according to either the second or third aspects.

Referring to the first aspect of the present invention, the monomer is a "pentamer". Such a "pentamer" has not been provided previously as part of a monomer for the preparation of a polymer.

For the purposes of the present application, the dashed circles in formula I or any other formula in the present application may be taken to indicate that each of the fused rings include sufficient double bonds in positions suitable to satisfy the valency of the atoms in the ring.

Preferably, each Ar group independently is substituted or unsubstituted and is selected from the group consisting of phenylene, thiophene, furan, pyridene, pyrrole, quinoxaline, benzothiadiazole, benzofuranodiazole, benzotriazole, and other diazines and 1,3,5 triazines. These preferred Ar groups include the following:

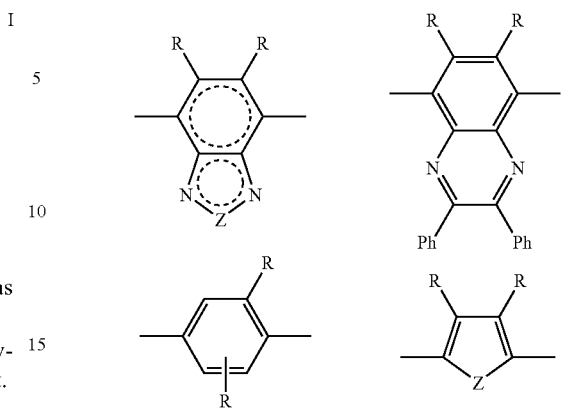

Z=S, O or N—R
R=H or a substituted group, preferably $C_{1-10}$ alkyl

Also, preferably each Ar group independently is substituted or unsubstituted and is a heteroaryl group.

A preferred monomer, having preferred Ar groups is a monomer having general formula II:

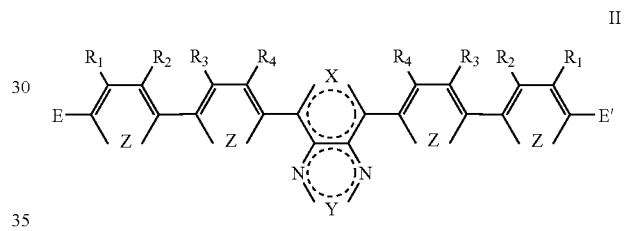

where E, E', X, Y, $R_5$, $R_6$, $R_7$ and $R_8$ are as defined above in relation to the first aspect of the present invention and each Z is the same or different and is independently O, S, NR or RC=CR and each R, $R_1$, $R_2$, $R_3$ and $R_4$ is the same or different from any one of the other R, $R_1$, $R_2$, $R_3$ and $R_4$ groups and each is independently H or a substituent group.

Preferred groups of general formula II are shown in general formulas III and IV:

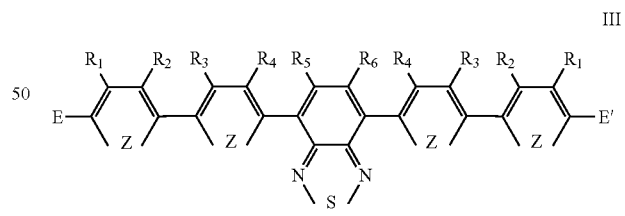

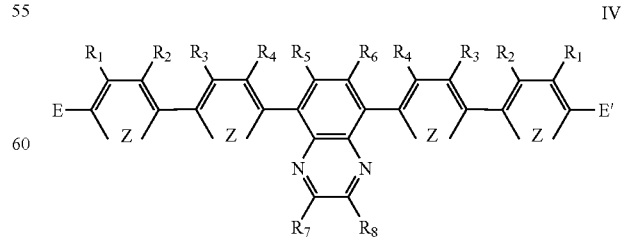

where E, E', Z, $R_1$, $R_2$, $R_3$, $R_4$, $R_5$, $R_6$, $R_7$ and Re are as defined above in relation to general formula II.

Preferred groups of general formula III are shown in general formula VIII to X, where $R_1$, $R_2$ and $R_3$ are substituent groups and E and E' are as defined in relation to general formula III.

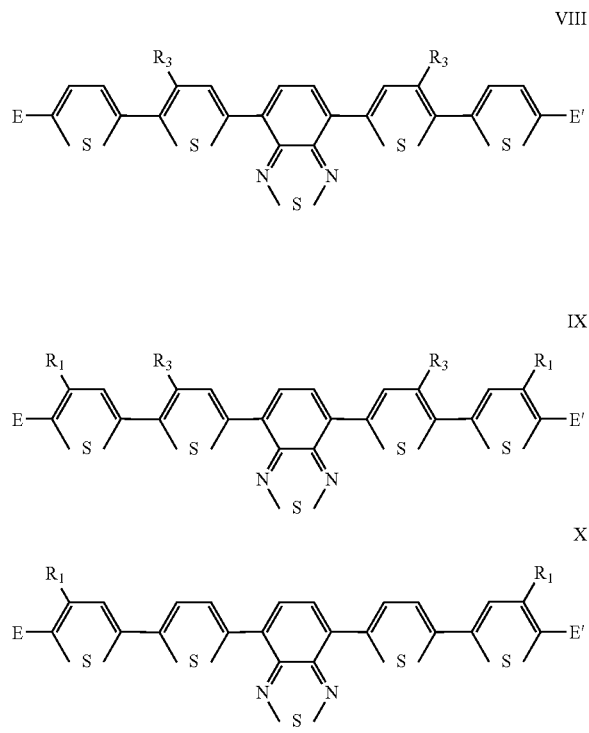

Preferred central groups of the "pentamer" in the first aspect include the following:

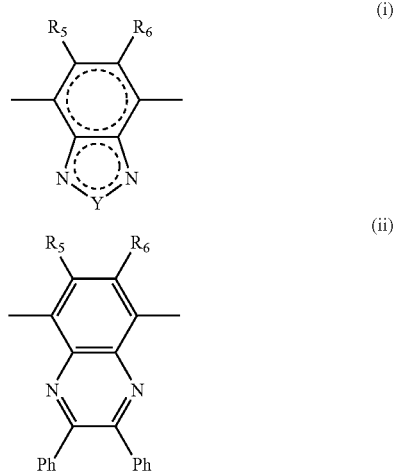

where Y=S, O or N—$R_7$ and $R_5$, $R_6$ and $R_7$ are the same or different and each independently is H or a substituent group, preferably H or $C_{1-10}$ alkyl or any other preferred substituent group defined in relation to general formulae II to IV. For ease of manufacture in central group (ii) above, the Ph substituents are positioned on the diazole ring rather than the benzene ring.

Referring to general formulae II, III, IV, VIII, IX and X, independently, preferred R, $R_1$, $R_2$, $R_3$, $R_4$, $R_5$, $R_6$, $R_7$ and $R_8$ groups include hydrogen or an optionally substituted hydrocarbyl group. The term "hydrocarbyl" is intended to include alkyl, alkenyl, alkynyl and aryl groups. A discussion of the effect of substituents on molecular orbital energy levels (HOMO and LUMO levels) can be found in Chapter 2 of Color Chemistry (Synthesis, Properties and Applications of Organic Dyes and Pigments) by Heinrich Zollinger ($2^{nd}$ edition, 1991, VCH Publishers, Inc., New York, N.Y. (USA)). Preferred substituents may be electron donating or electron withdrawing substituents depending on the preferred effect on the bandgap of a polymer prepared from the monomer. Other preferred substituents include solubilising groups i.e. a substituent that improves the solubility in a common organic solvent, toluene, xylene or THF of a polymer derived from the monomer.

Independently, preferred R, $R_1$, $R_2$, $R_3$, $R_4$, $R_5$, $R_6$, $R_7$ and $R_8$ substituent groups include amine, cyano, alkyl, aryl, heteroaryl, alkoxy, thioalkyl, perhaloalkyl, alkylaryl, arylalkyl, alkyloxy, aryloxy, alkoxyaryl or alkoxy heteroaryl groups.

In a particularly preferred embodiment, at least one or more than one of the $R_1$, $R_2$, $R_3$ and $R_4$ groups is an unsubstituted $C_{1-10}$, alkyl or alkoxy group. Such groups will increase the solubility of such a polymer.

Thus, in general formulae III, VIII, IX or X, independently, preferred $R_1$, $R_2$, $R_3$ and $R_4$ groups and also preferred $R_5$ and $R_6$ groups include hydrogen and $C_{1-10}$, alkyl or alkoxy. As mentioned above $C_{1-10}$, alkyl or alkoxy group substituents can be used to improve the solubility of a polymer derived from the monomer. Furthermore, the electronic properties of the hydrogen or $C_{1-10}$, alkyl or alkoxy group substituents are useful in selecting the bandgap of a polymer derived from the monomer. Suitably, $C_{1-10}$ alkyl or alkoxy substituent groups are provided on the inner Ar groups.

In general formula IV, it is preferred that $R_7$ and $R_8$ are the same and are both a substituted or unsubstituted phenyl group.

As mentioned above, in the present monomer, each Ar group may be the same or different. However, for ease of manufacture, it is preferred that each Ar is the same.

It is preferred that one or more of the Ar groups comprises one or more solubilising group substituents.

In the monomer according to the first aspect of the present invention, it is preferred that E and $E^1$ are the same or different and are selected from the group consisting of a reactive halide functional group and a reactive boron derivative group. Specifically, the reactive halide functional group is selected from the group consisting of F, Cl, Br and I and the boron derivative group is selected from the group consisting of a boronic acid group, a boronic ester group and a borane group.

The use of a monomer according to the first aspect of the present invention for the preparation of a polymer is provided. Typically, the polymer will be provided as a component, preferably a light-emissive component, in an optical device.

According to the second aspect of the present invention a polymer prepared from a monomer as defined above in the first aspect of the present invention is provided.

Also, in the third aspect of the present invention there is provided a polymer comprising a first repeat unit comprising a unit having general formula V which is substituted or unsubstituted:

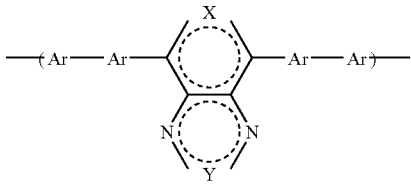

V where X, Y and Ar are as defined above in relation to the first aspect of the present invention, with the proviso that none of the Ar groups comprise a mono fluorene group. The nature of a mono fluorene group is such that a polymer comprising a first repeat unit comprising a unit having general formula V where one or more of the Ar groups comprised a mono fluorene group would not have a very low bandgap as will be typical for many polymers according to the second aspect of the present invention.

For the purposes of the present invention, the term a "mono fluorene" group may be taken to include any substituted or unsubstituted group as shown below:

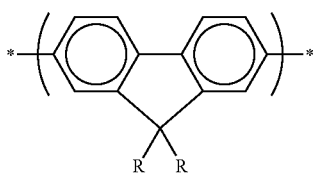

where each R independently is H or a substituent group and each * indicates a linking position linking the fluorene group to the polymer chain and the fluorene group is not linked at either linking position to another fluorene group. Mono fluorene groups are excluded because they do not allow useful tuning of the polymer's electronic and physical properties. A mono-fluorene group in the polymer backbone simply can be viewed as a linker group that is not capable of usefully tuning the polymer's electronic and physical properties for the purposes of the present invention. Furthermore, polymers having mono-fluorene groups in the polymer chain tend to have a lower Tg and also are prone to aggregation.

In a further embodiment of the third aspect of the present invention, none of the Ar groups comprise a fluorene group.

It has been found that in a polymer having a repeat unit derived from a monomer according to the first aspect of the present invention, the arrangement of the substituted or unsubstituted aryl or heteroaryl groups (Ar groups) leads to a polymer having a lower bandgap as compared with a polymer derived from a 'trimer' monomer having general formula:

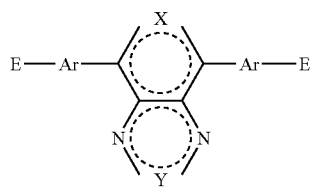

This lowering of the bandgap is extremely useful for preparing polymers having a very low bandgap, for example, capable of emitting radiation in the IR region. Furthermore, it is extremely useful for overcoming to some extent the sacrifice in emission colour which may result from the inclusion of solubilising moieties in the polymer derived from the above 'trimer' monomer.

Polymers according to the second or third aspect of the present invention will have a wider range of possible emission wavelengths as compared with a polymer derived from the above 'trimer' monomer and thus will have a wider field of application, beyond the field of electroluminescent display devices.

In a preferred embodiment of the second or third aspect of the present invention, the polymer comprises a second repeat unit $Ar_1$ that is a substituted or unsubstituted aryl or heteroaryl group. It is preferred that, in a polymer comprising a second repeat unit $Ar_1$, the polymer comprises a repeat unit having formula VI that is substituted or unsubstituted:

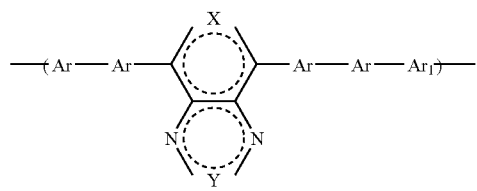

VI $Ar^1$ may be selected from the group consisting of a substituted or unsubstituted, fused or unfused, benzene, thiophene, furan, fluorene, triarylamine, bistriarylamine or pyridine group. More preferably, the second repeat unit is selected from the group consisting of a 2,3-, 2,5- or 2,6-substituted benzene; 3,4-substituted thiophene; 3,4-substituted furan; 9,9-disubstituted fluorene; unsubstituted pyridine; benzo-, thio-, or furano-2,3-substituted diazine; unsubstituted phenothiadiazine or an unsubstituted triarylamine or bistriarylamine group.

Polymers according to the second or third aspect of the present invention may comprise a homopolymer, copolymer, terpolymer or higher order polymer. In this regard, a repeat unit is distinguished from a residual monomeric unit. A homopolymer (i.e. prepared by polymerisation of a single type of monomer) may be defined to have more than one different repeat unit. Where the polymer is not a homopolymer, it may be a random or regular alternating polymer.

Where the present polymer is a copolymer, it is preferred that it is a 1:1 copolymer. A preferred comonomer in a copolymer comprises a fluorene group.

Further preferred polymers according to the second and third aspects of the present invention further comprise a third repeat unit $Ar_2$ that is a substituted or unsubstituted aryl or heteroaryl group. A preferred third repeat unit has general formula VII that is substituted or unsubstituted:

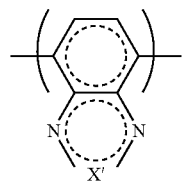

VII where X' is O or S. A particularly preferred polymer in this regard has a repeat unit as shown in general formula VI and a repeat unit as shown in general formula VII.

Generally, it is preferred that a polymer according to the second or third aspect of the present invention comprises up to about 50 mol % of a unit having general formula V. More preferably, the polymer will comprise from 0.1 mol % to 50 mol %, more preferably from 5 mol % to 10 mol % of the unit.

As mentioned above, the components of a polymer according to the second or third aspect of the present invention, can be selected so that the polymer has a very low bandgap. Such polymers are particularly useful since many are capable of emitting light at a wavelength in the range 550 nm to 1000 nm, particularly 700 to 800 nm or 800 to 1000 nm.

From the nature of the first repeat unit, it will be clear that at least a part of the backbone of a polymer according to the second or third aspect of the present invention will be conjugated. Preferably, the polymer backbone will be partially, substantially, or even fully conjugated.

A polymer according to the second or third aspect of the present invention will have a degree of polymerisation of at least 3.

Typically, a polymer according to the second or third aspect of the present invention will have a molecular weight of at least $M_n$=about 10,000 daltons. Preferably, they will have an average molecular weight in the range 10,000 to $10^6$.

Typically, a polymer according to the second or third aspect of the present invention will be soluble in common organic solvents such as toluene, xylene and THF. Such polymers conveniently can be laid down as a film from solution.

Accordingly, a film comprising a polymer according to the second or third aspect of the present invention also is provided.

Furthermore, a coating comprising a polymer as defined in the first or second aspect of the present invention is provided.

Still further, a composition comprising a mixture which comprises a polymer as defined in the first or second aspect of the present invention is provided. Preferably, the mixture comprises one or two further, different polymers.

A polymer according to the second or third aspect of the present invention is envisaged to be useful as a component in an optical device, particularly a light-emitting device. A particularly preferred use is as a component in an electroluminescent device.

The very low bandgap that is obtainable for a polymer according to the second or third aspect of the present invention means that the polymer also may be used as a component in a photovoltaic device or optoelectronic device such as a solar cell. It also may be used in an infra-red emitting polymer LED such as a sensor, remote control, detector.

Other uses include the use of the polymer as a component in a photoluminescent device, a waveguide, a dye composition, a sensor, an electrochemical cell or a fibre.

In this regard, the present invention also provides the use of a repeat unit having general formula V that is substituted or unsubstituted for accepting and combining positive and negative charge carriers to generate light in a part of a polymer.

According to a sixth aspect of the present invention, there is provided a method for making a polymer according to the second or third aspect of the present invention which includes the step of reacting in a reaction mixture a first monomer and a second monomer. The first and second monomers may be the same or different from one another. Further steps may involve a reaction with further monomers.

Several different polymerisation methods are known which may be used to manufacture polymers in accordance with the second and third aspects of the present invention.

One particularly suitable method is disclosed in International patent publication No. WO 00/53656, the contents of which are incorporated herein by reference. This describes the process for preparing a conjugated polymer, which comprises polymerising in a reaction mixture (a) an aromatic monomer having at least two reactive boron derivative groups selected from a boronic acid group, a boronic ester group and a borane group, and an aromatic monomer having at least two reactive halide functional groups, or (b) an aromatic monomer having one reactive halide functional group and one reactive boron derivative group selected from a boronic acid group, a boronic ester group and a borane group, wherein the reaction mixture comprises a catalytic amount of a catalyst (e.g. palladium) suitable for catalysing the polymerisation of the aromatic monomers, and an organic base in an amount sufficient to convert the reactive boron derivative functional groups into active polymerisable units, particularly —$BX_3^-$ anionic groups, wherein X is independently selected from the group consisting of F, alkoxy and OH.

Polymers according to the present invention which have been produced by this method are particularly advantageous. This is because reaction times are short and residual catalyst (e.g. palladium) levels are low.

Another polymerisation method is disclosed in U.S. Pat. No. 5,777,070. The process involves contacting monomers having two reactive groups selected from boronic acid, C1-C6 boronic acid ester, C1-C6 borane and combinations thereof with aromatic dihalide functional monomers or monomers having one reactive boronic acid, boronic acid ester or borane group and one reactive halide functional group with each other.

A further polymerisation method is known from "Macromolecules", 31, 1099-1103 (1998). The polymerisation reaction involves nickel-mediated coupling of dibromide monomers. This method commonly is known as "Yamamoto Polymerisation".

According to one embodiment of the sixth aspect of the present invention there is provided a process for preparing a polymer as defined above in relation to the second or third aspect of the present invention which includes polymerising in a reaction mixture:

(a) a first aromatic monomer comprising a first repeat unit as defined above in general formula V and at least two reaction boron derivative groups selected from a boronic acid group, a boronic ester group and a borane group; and (b) a second aromatic monomer comprising further of the first repeat unit and/or a second repeat unit $Ar_1$ and at least two reactive halide functional groups, wherein each boron derivative group is selected from a boronic acid group, a boronic ester group and a borane group and wherein the reaction mixture comprises a catalytic amount of a catalyst suitable for catalysing the polymerisation of the aromatic monomers, and an organic base in an amount sufficient to convert the reactive boron derivative functional groups into —$BX_3^-$ anionic groups, wherein X is independently selected from the group consisting of F, alkoxy and OH.

A further process according to the sixth aspect of this invention for preparing a polymer as defined above in relation to the second or third aspect of the present invention also is provided which includes polymerising in a reaction mixture:

(a) a first aromatic monomer comprising a first repeat unit as defined above in general formula V and one reactive halide functional group and one reactive boron derivative group; and (b) a second aromatic monomer comprising further of the first repeat unit and/or a second repeat unit $Ar_1$, and one reactive halide functional group and one reactive boron derivative group, wherein each boron derivative group is selected from a boronic acid group, a boronic ester group and a borane group and wherein the reaction mixture comprises a catalytic amount of a catalyst suitable for catalysing the polymerisation of the aromatic monomers, and an organic base in an amount sufficient to convert the reactive boron derivative functional groups into $-BX_3^-$ anionic groups, wherein X is independently selected from the group consisting of F, alkoxy and OH.

In a final aspect of the present invention, there is provided an optical device or a component therefore, which comprises a substrate and a polymer according to the second or third aspect supported on the substrate.

A device according to the present invention may be prepared in accordance with the disclosure of WO 99/48160, the contents of which are incorporated herein by reference. Polymers according to the second or third aspect of the present invention may be present in the device as the sole light emitting polymer or as a component in a blend further comprising hole and/or electron transporting polymers. Alternatively, the device may comprise distinct layers of a polymer of the present invention, a hole transporting polymer and/or an electron transporting polymer.

In one embodiment, the optical device comprises an electroluminescent device. Specifically, the electroluminescent device comprises a first charge injecting layer for injecting positive charge carriers, a second charge injecting layer for injecting negative charge carriers, a light-emissive layer located between the first and second charge injecting layers comprising a light-emissive material for accepting and combining positive and negative charge carriers to generate light wherein the light-emissive layer comprises a polymer as defined in the first or second aspects for accepting and combining positive and negative charge carriers or for transporting positive and/or negative charge carriers from the first and/or second charge injecting layer to the light-emissive material. In one embodiment, the polymer according to the present invention is provided as the light-emissive material.

It will be appreciated that the light-emissive layer may be formed from a blend or mixture of materials including one or more polymers according to the present invention, and optionally further different polymers. As mentioned above, usually, the polymer according to the present invention will be included for accepting and combining positive and negative charge carriers to generate light. The further different polymers may be so-called hole transport polymers (i.e. to improve the efficiency of hole transport to the light-emissive material) or electron-transport polymers (i.e. to improve the efficiency of electron-transport to the light-emissive material). Preferably, the blend or mixture would comprise at least 0.1% by weight of a polymer according to the present invention, preferably from about 0.2 to about 50% more preferably from about 0.5% to about 30% by weight.

Alternatively, a polymer according to the present invention may be provided in an electroluminescent device as discrete layer situated between the first and second charge injecting layers. Where this discrete layer is included for accepting and combining positive and negative charge carriers to generate light it optionally may be in contact with one or more hole and/or electron transporting layers.

The present invention now will be described in further detail with reference to the attached drawing in which.

Figure 1:
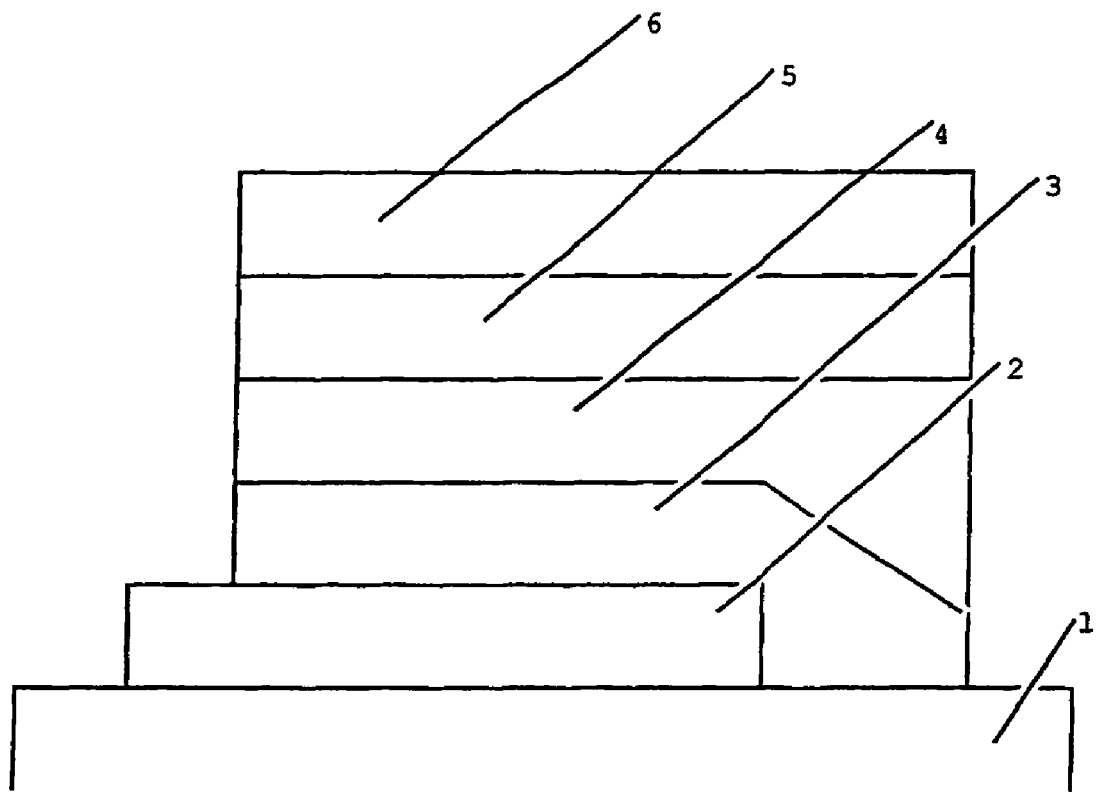
FIG. 1 is a schematic diagram of an electroluminescent device according to this invention.

"Pentamer" monomers of formula I may be prepared from the "trimer" monomers disclosed in WO 00/46321 and in PCT/GB01/00019 (incorporated herein by reference). Pentamer monomers may be prepared by essentially the same methodology used to generate the "trimer" monomers disclosed in this prior art, as outlined below:

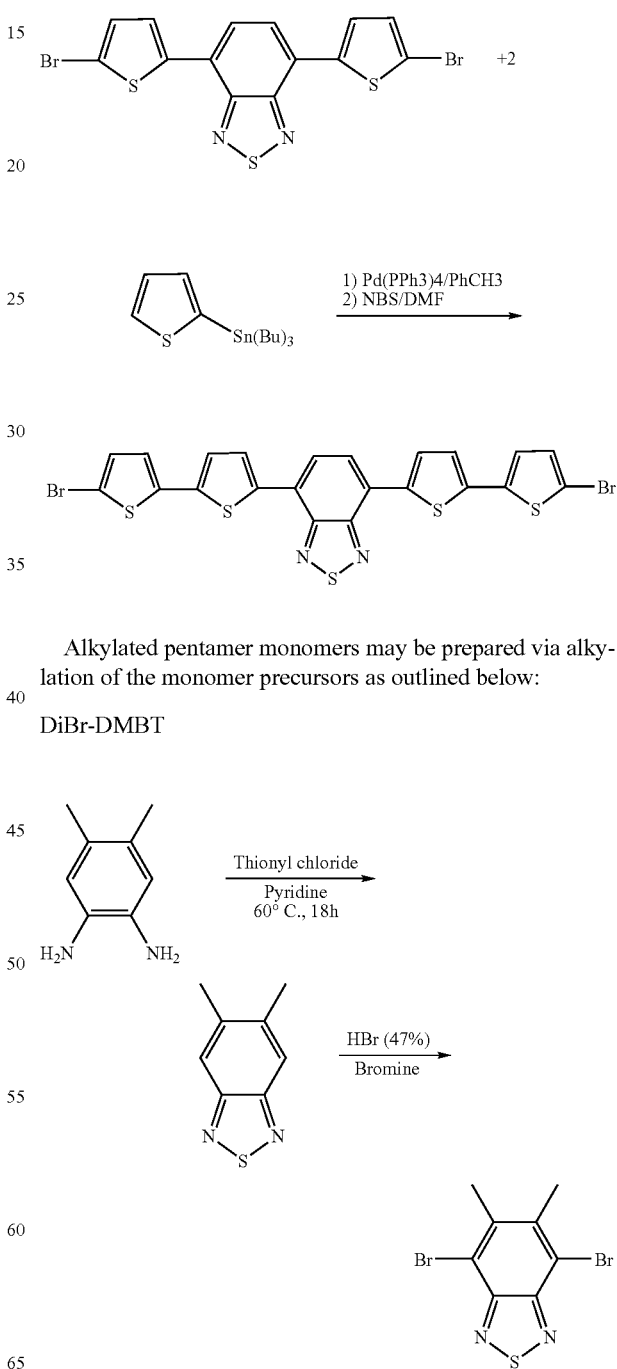

Alkylated pentamer monomers may be prepared via alkylation of the monomer precursors as outlined below:

DiBr-DMBT

DiBr-MBT
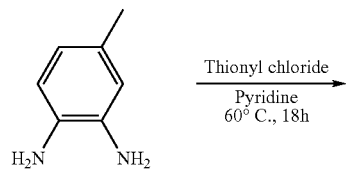
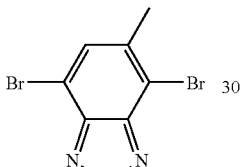
3-Hexyl Thiophene
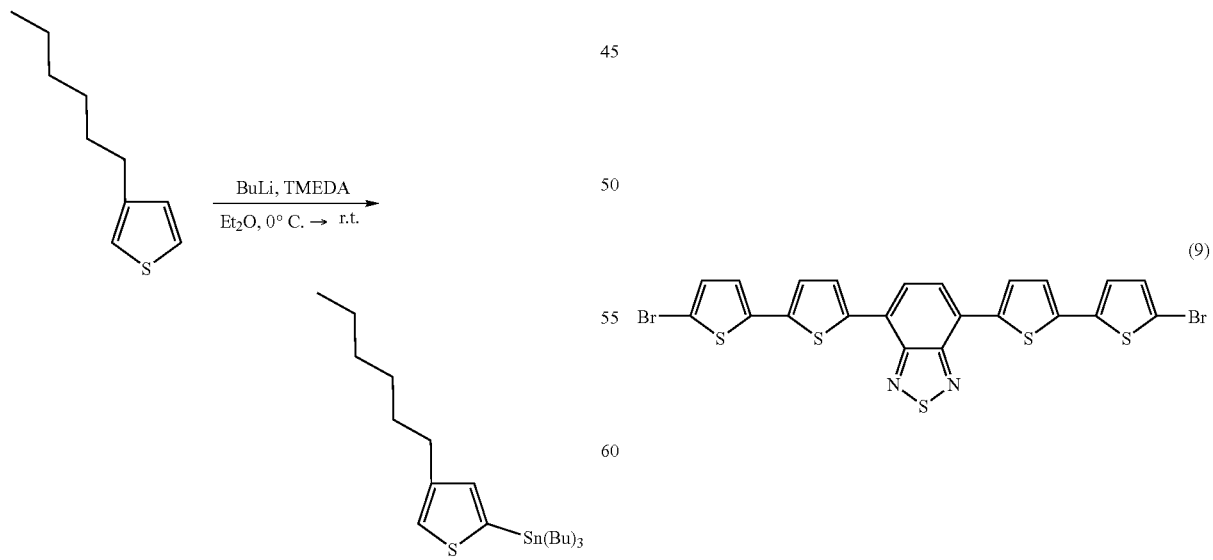
Polymers according to the present invention may be prepared by Suzuki polymerisation as disclosed in WO 00/53656 (incorporated herein by reference). In one particular example, the polymer is prepared from monomers 7, 8 and 9 shown below present in a ratio of 50:25:25.
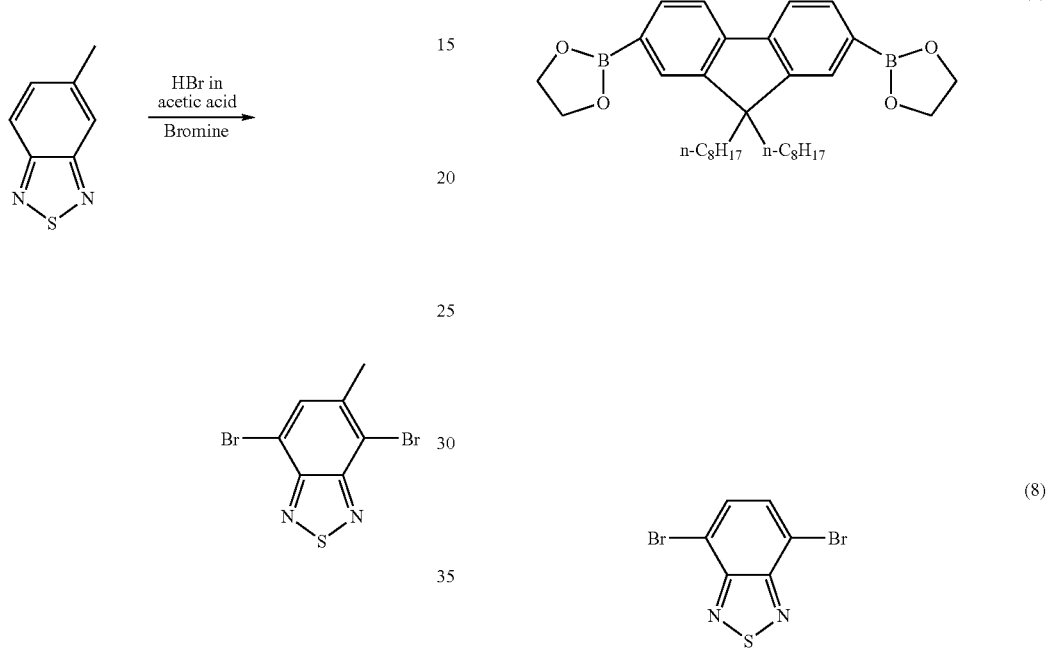
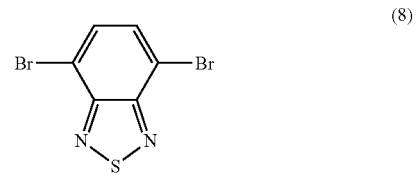
Alternatively, the polymer may consist of a 1:1 co-polymer of dioctylfluorene and a pentamer.

EXAMPLE 1

Preparation of Pentamer Monomers

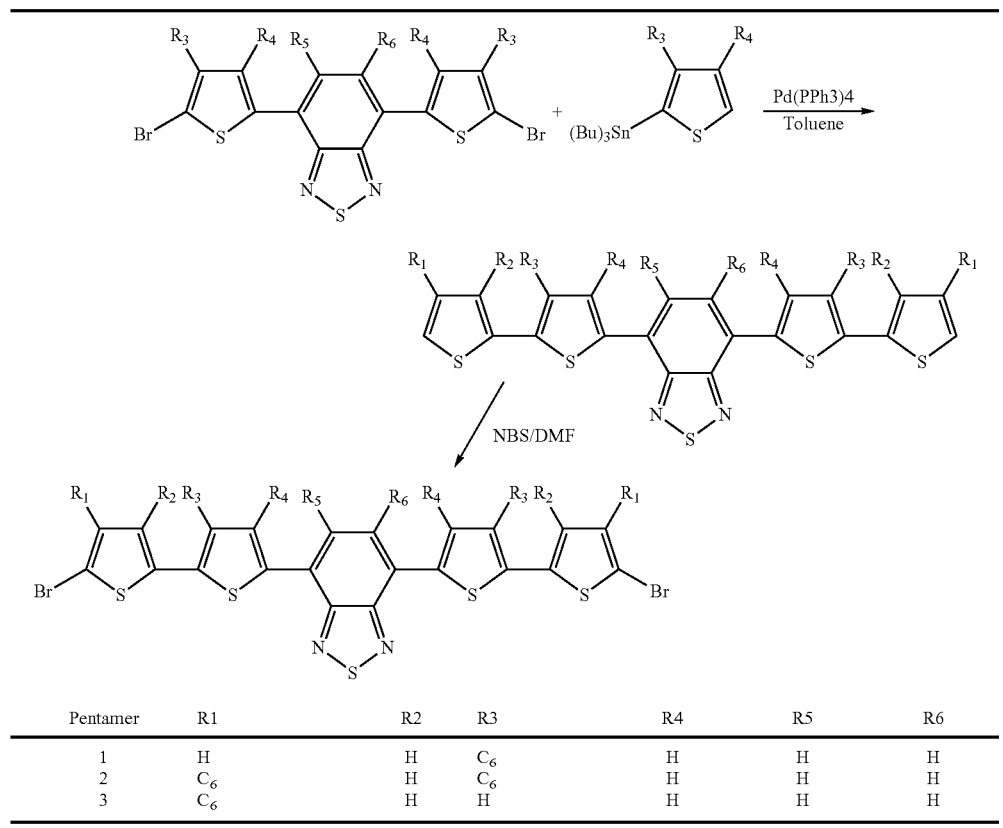

| Pentamer | R1 | R2 | R3 | R4 | R5 | R6 |
|---|---|---|---|---|---|---|
| 1 | H | H | $C_6$ | H | H | H |
| 2 | $C_6$ | H | $C_6$ | H | H | H |
| 3 | $C_6$ | H | H | H | H | H |

(A) Synthesis of Pentamer 1

Step 1 (Stille-Coupling)

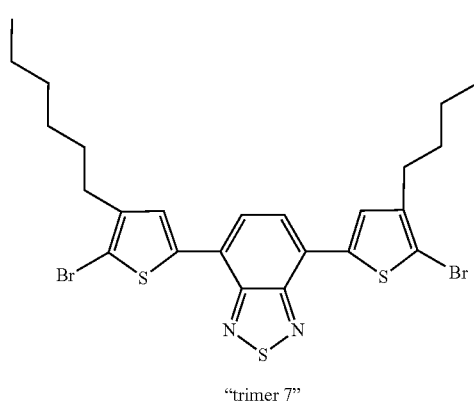

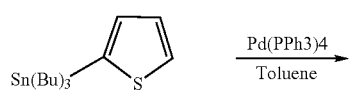

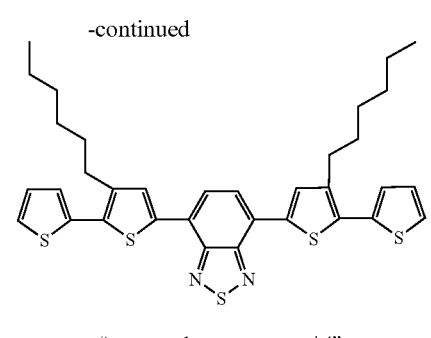

"pentamer 1 precursor material"

Trimer 7 was prepared in accordance with the method disclosed in WO 01/49768.

2-(Tributylstannyl)thiophene (22.34 g, 59.9 mmol), trimer 7 (15.00 g, 23.9 mmol), and tetrakis(triphenyl-phosphine) palladium (0) (0.55 g,. 2 mol %) in toluene (200 mL) was refluxed. The reaction was followed by tlc. (hexane eluent) After 18 h, the reaction was allowed to cool to room temperature and was then filtered through silica. The filtrate was evaporated to dryness and recrystalised from hexane to give 10.7 g (70.7% yield, $^1$H nmr (CDCl$_3$/TMS) 7.98 (2H, s); 7.82 (2H, s); 7.34 (2H, dd); 7.23 (2H, dd); 7.10 (2H, dd); 2.78 (H4, t, J=7.8); 1.75-1.26 (20H); 0.91 (H6, t, J=7.2). 99.6% by HPLC).

Step 2 (NBS bromination)

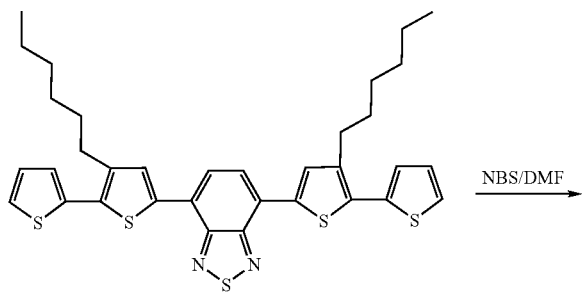

NBS/DMF

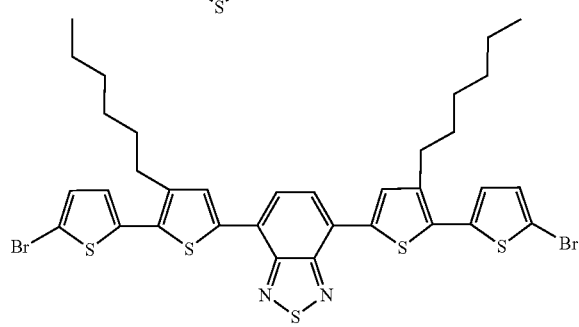

A suspension of the pentamer 1 precursor material (10.7 g, 16.9 mmol) in DMF (200 mL) was dissolved by gentle heating. The solution was allowed to cool to r.t. before starting dropwise addition (in the absence of light) of N-bromosuccinimide (6.0 g, 33.8 mmol) in DMF (50 mL). The reaction was stirred overnight before the product was filtered off and washed (methanol, deionised water). Recrystallisation from hexane gave 6.3 g (47% yield). Further material was obtained from recystallisation of the mother liquor. $^1$H nmr (CDCl$_3$/TMS) 7.93 (2H, s); 7.78 (2H, s); 7.01 (4H, dd,); 2.78 (H4, t, J=7.8); 1.75-1.26 (20H); 0.91 (H6, t, J=7.2). 99.6% by HPLC).

(B) Synthesis of Pentamer 2

Step 1 (Stille-Coupling)

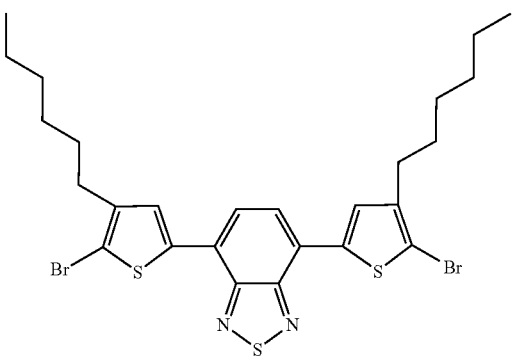

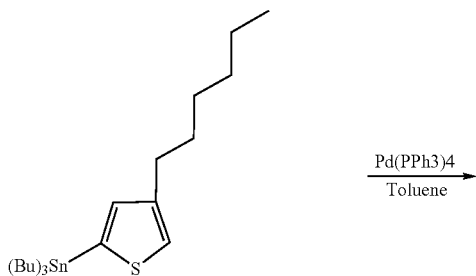

Pd(PPh3)4
Toluene

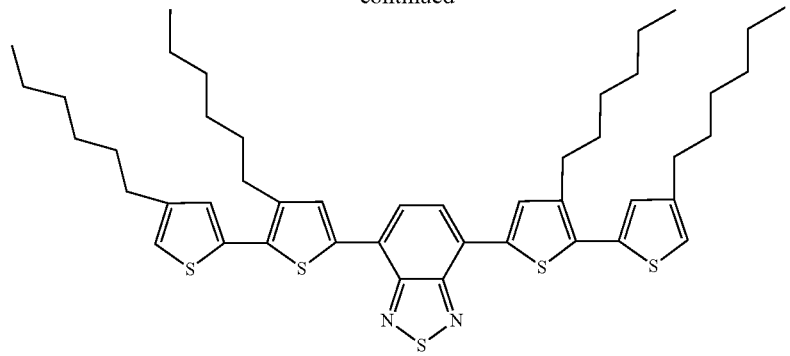

3-Hexyl-5-tributylstannylthiophene (32.8 g, 71.8 mmol), trimer 7 (15.0 g, 23.9 mmol), and tetrakis(triphenyl-phosphine) palladium (0) (0.55 g, 2 mol %) in toluene (200 mL) was refluxed. The reaction was followed by tlc. (hexane eluent) After 18 h, the reaction was allowed to cool to room temperature and was then filtered through silica. The filtrate was evaporated to dryness and recrystalised from IPA to give 15.8 g (82.4% yield).

Step 2 (NBS bromination)
This material was brominated identically as described for Pentamer 1 in Example 1(A).

(C) Pentamer 3
This pentamer was prepared using same methods as pentamers 1 and 2 in Examples 1(A) and 1(B).

Step 1 (Stille-coupling)
Yield 15.2g, 73.3%. $^1$H nmr (CDCl$_3$/TMS) 8.02 (2H, d); 7.83 (2H, s); 7.23 (2H, d); 7.14 (2H, s); 6.85 (2H, s); 2.59 (H4, t); 1.90-1.28 (20H); 0.91 (H6, t).

Step 2 (NBS bromination)
Yield 13.4 g, 71.5%. $^1$H nmr (CDCl$_3$/TMS) 7.99 (2H, d, J=4.0); 7.82 (2H, s); 7.16 (2H, d, J=4.0); 6.98 (2H, s); 2.56 (H4, t, J=8.0); 1.64-1.26 (20H); 0.91 (H6, t, J=8.0)

EXAMPLE 2

Preparation of Polymers
A polymer according to the invention was prepared according to the method of W000/53656, in the presence of 10 mol % bromothiophene to limit molecular weight, by reaction of 9,9-di-n-octylfluorene-2,7-diethyleneboronate (1.9132 g, 3.6

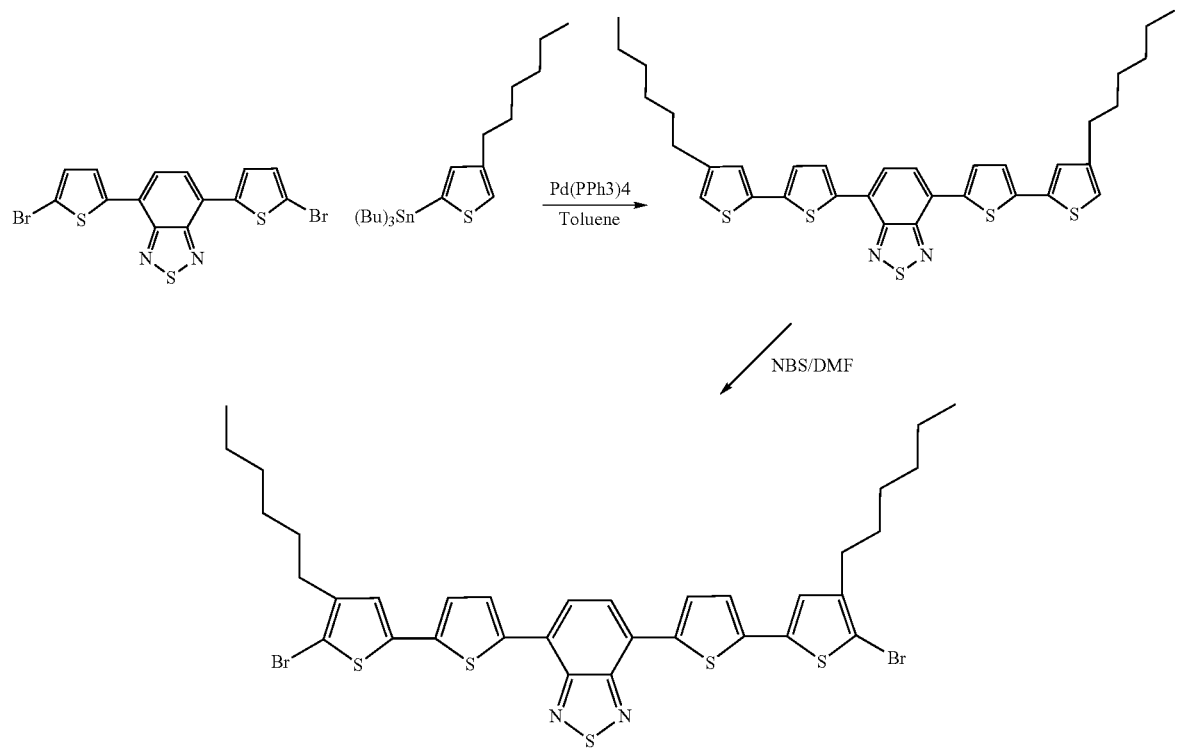

mmol) and pentamer 1 (2.8526 g, 3.6 mmol) in toluene (40 ml). The crude polymer was passed through a celite column, eluted with toluene and precipitated in methanol to furnish the final polymer (9,9-di-n-octylfluorene-Pentamer 1). Final Mp~23,000.

EXAMPLE 3

Electroluminescent Device

A suitable device structure is shown in FIG. 1. The anode 2 is a layer of transparent indium-tin oxide ("ITO") supported on a glass or plastic substrate 1. The anode 2 layer has a thickness between 1000-2000 Å, usually about 1500 Å. The cathode 5 is a Ca layer having an approximate thickness of 1500 Å. Between the electrodes is a light emissive layer 4 having a thickness up to about 1000 Å. The emissive layer 4 comprises between 0.5 to 30% by weight of the present polymer with the remainder of the emissive layer consisting of hole and/or electron transport material and/or emissive material. Advantageously, the device includes a hole transport material layer 3 of PEDOT having a thickness of about 1000 Å. Layer 6 is an encapsulant layer of a suitable thickness.

Experiment 1

Photovoltaic Application

An effective form of photovoltaic devices is that comprising a blend of an electron donor such as poly(3-hexylthiophene) (P3HT) and an electron acceptor such as F8-trimer copolymer (below) as the active materials. Photovoltaic devices comprising blends are discussed in U.S. Pat. No. 5,670,791.

In these devices, excitons formed on F8-trimer are ionized by transfer of a hole to the P3HT, whereas excitons formed on P3HT are dissociated by transfer of an electron to F8-trimer:

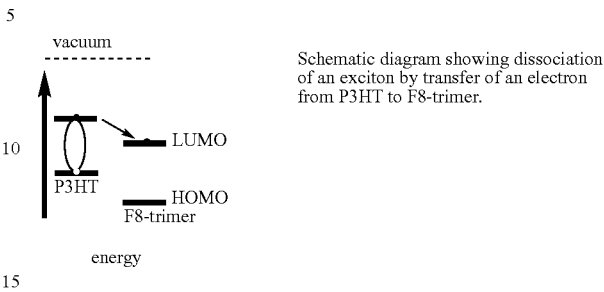

Schematic diagram showing dissociation of an exciton by transfer of an electron from P3HT to F8-trimer.

A drawback of these blends with respect to their use as solar cells is that they do not absorb a significant fraction of solar radiation. However polymers according to the present invention absorb a significantly larger proportion of radiation as illustrated by comparison of absorption spectra of a blend of P3HT and F8-trimer copolymer with a blend of P3HT and polymer F8-pentamer 1 according to the present invention. The absorption spectra are shown in FIG. 2.

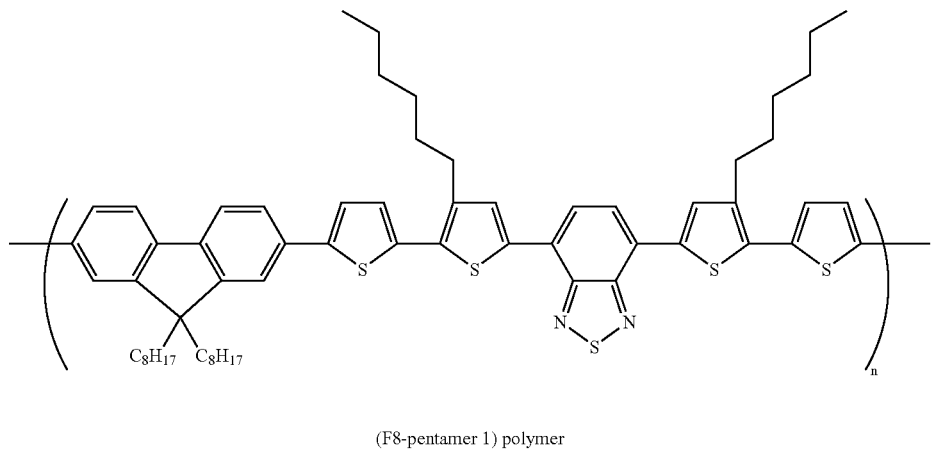

(F8-pentamer 1) polymer

Figure 2:
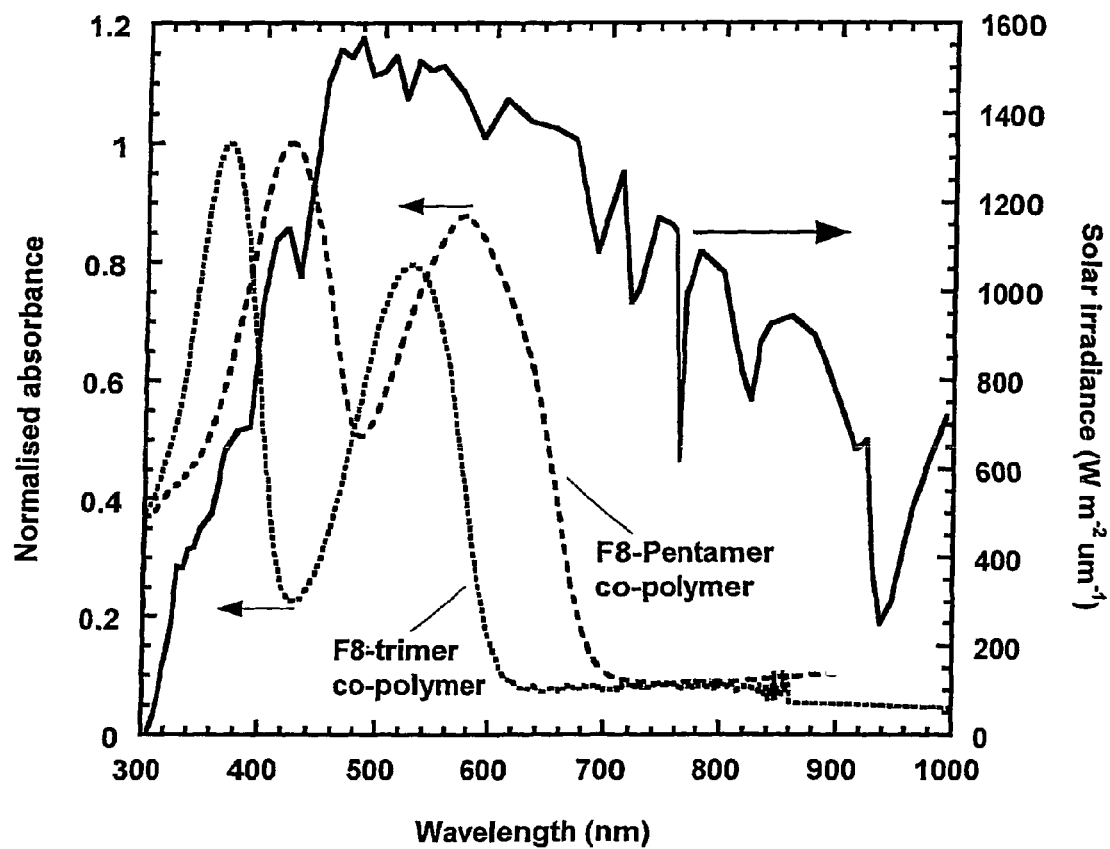
FIG. 2 shows absorption spectra.

In FIG. 2, the full line shows solar irradiance at the Earth's surface. The onset of absorption for the trimer containing copolymer is around 610 nm (dotted line) whereas the onset of absorption for the pentamer copolymer is red-shifted by about 75 nm to around 685 nm (dashed line).

Experiment 2

PLED Application

Figure 3:
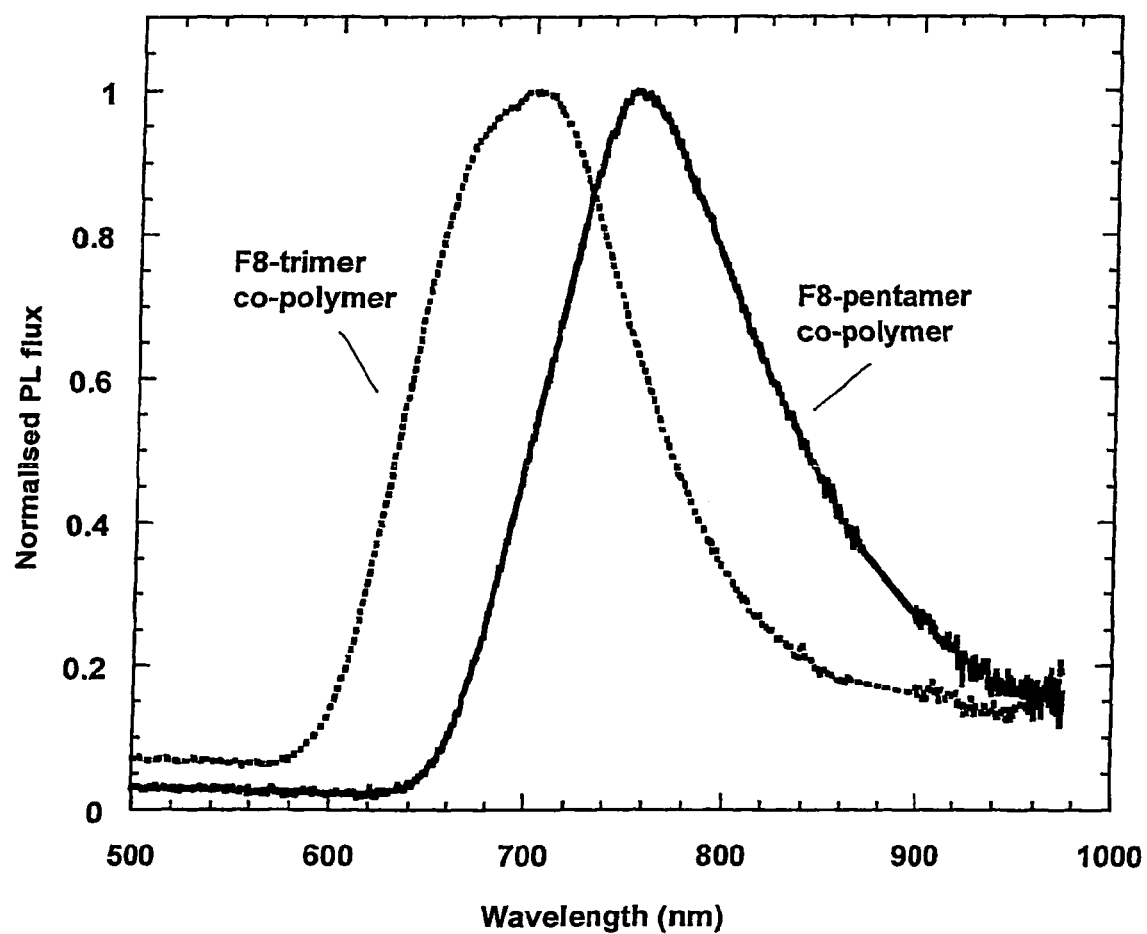
FIG. 3 shows photoluminescence spectra.

As can be seen from the photoluminescence spectra shown in FIG. 3, the luminescence of the F8-pentamer 1 copolymer is red-shifted by comparison with the F8-trimer copolymer.

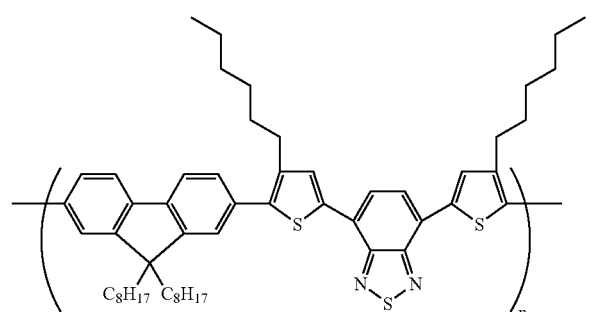

"F8"       "trimer"

The invention claimed is:

1. A monomer having general formula I which may be substituted or unsubstituted:

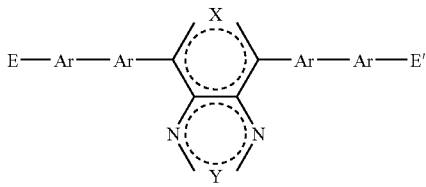

where E and E' are the same or different and are reactive groups capable of undergoing chain extension; X is O, S, $NR_5$, $R_5C$—$CR_6$ or $R_5C$=$CR_6$; Y is O, S, $NR_7$, $R_7C$—$CR_8$ or $R_7C$=$CR_8$; $R_5$, $R_6$, $R_7$ and $R_8$ are the same or different and each is independently H or a substituent group; each Ar is the same or different and is independently a substituted or unsubstituted aryl or heteroaryl group; and the reactive groups are selected from reactive halide functional groups and reactive boron derivative groups.

2. A monomer according to claim 1, wherein each Ar independently is substituted or unsubstituted and is selected from the group consisting of phenylene, thiophene, furan, pyridine, pyrrole, quinoxaline, benzothiadiazole, benzofuranodiazole, benzotriazole, other diazines and 1,3,5 triazines.

3. A monomer according to claim 2, having general formula II:

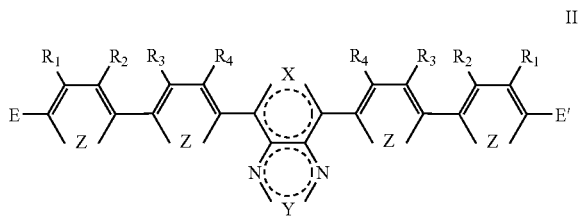

where E, E', X, Y, $R_5$, $R_6$, $R_7$ and $R_8$ are as defined in claim 1 and each Z is the same or different and is independently O, S, NR or RC=CR and R, $R_1$, $R_2$, $R_3$ and $R_4$ are the same or different and each is independently H or a substituent group.

4. A monomer according to claim 3, having general formula III:

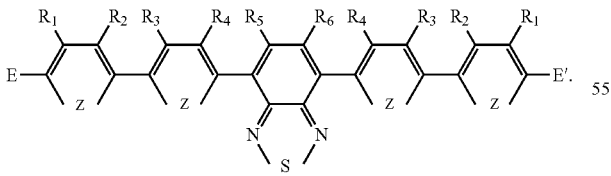

5. A monomer according to claim 3, where each Z is the same or different and is independently S or O.

6. A monomer according to claim 4, where each Z is the same or different and is independently S or O.

7. A monomer according to claim 1, where at least one Ar comprises at least one $C_{1-10}$ alkyl or $C_{1-10}$ alkoxy substituent group.

8. A monomer according to claim 1, where the reactive halide functional group is selected from the group consisting of F, Cl, Br or I and the boron derivative group is selected from the group consisting of a boronic acid group, a boronic ester group or a borane group.

9. A polymer prepared from a monomer as defined in claim 1.

10. A polymer according to claim 9, capable of emitting light at a wavelength in the range 550 nm to 1000 nm.

11. A polymer according to claim 9, wherein the polymer backbone is fully conjugated.

12. Optical device including a component comprising a polymer as defined in claim 9.

13. An optical device or a component therefor, which comprises a substrate and a polymer according to claim 9 supported on the substrate.

14. An optical device according to claim 13, wherein the optical device comprises an electroluminescent device.

15. An optical device according to claim 14, wherein the electroluminescent device comprises:
   a first charge injecting layer for injecting positive charge carriers;
   a second charge injecting layer for injecting negative charge carriers;
   a light-emissive layer located between the first and second charge injecting layers comprising a light-emissive material for accepting and combining positive and negative charge carriers to generate light:
   wherein the light-emissive material comprises said polymer.

16. A polymer according to claim 9 further comprising a second repeat unit $Ar_1$ that is a substituted or unsubstituted aryl or heteroaryl group.

17. A polymer according to claim 16 further comprising a third repeat unit $Ar_2$ that is a substituted or unsubstituted aryl or heteroaryl group.

18. A polymer according to claim 17, where at least one of $Ar_1$ and $Ar_2$ comprises a substituted or unsubstituted fluorene group or a substituted or unsubstituted benzothiadiazole group.

19. A polymer comprising a first repeat unit and a second repeat unit $Ar_1$, the first repeat unit comprising a unit having general formula V that is substituted or unsubstituted:

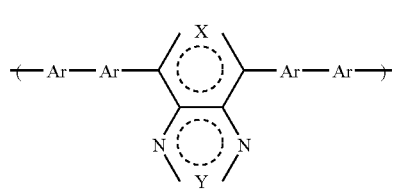

where X is O, S, $NR_5$, $R_5C$—$CR_6$ or $R_5C$=$R_6$; Y is O, S, $NR_7$, $R_7C$—$CR_8$ or $R_7C$=$CR_8$; $R_5$, $R_6$, $R_7$ and $R_8$ are the same or different and each is independently H or a substituent group; and each Ar is the same or different and is independently a substituted or unsubstituted aryl or heteroaryl group, and provided that none of the Ar groups comprise a mono fluorene group,
and the second repeat unit $Ar_1$ is a substituted or unsubstituted aryl or heteroaryl group.

20. A polymer according to claim 19, wherein each Ar is the same or different and each independently is a substituted or unsubstituted heteroaryl group.

21. A polymer according to claim 19, capable of emitting light at a wavelength in the range 550 nm to 1000 nm.

22. A polymer according to claim 19, wherein the polymer backbone is fully conjugated.

23. A polymer according to claim 19 further comprising a third repeat unit Ar$_2$ that is a substituted or unsubstituted aryl or heteroaryl group.

24. A polymer according to claim 23, where at least one of Ar$_1$ and Ar$_2$ comprises a substituted or unsubstituted fluorene group or a substituted or unsubstituted benzothiadiazole group.

25. A method for making a polymer which includes the step of polymerizing in a reaction mixture:
   (a) a first aromatic monomer comprising a first repeat unit as defined in general formula V, the first aromatic monomer containing either (i) at least two reactive boron derivative groups selected from a boronic acid group, a boronic ester group and a borane group or (ii) at least two reactive halide functional groups; and
   (b) a second aromatic monomer comprising further of the first repeat unit and/or a second repeat unit Ar$_1$ that is a substituted or unsubstituted aryl or heteroaryl group, the second aromatic monomer containing the other of (i) at least two reactive boron derivative groups selected from a boronic acid group, a boronic ester group and a borane group and (ii) at least two reactive halide functional groups,
   wherein the reaction mixture comprises a catalytic amount of a catalyst suitable for catalyzing the polymerization of the aromatic monomers, and an organic base in a amount sufficient to convert the reactive boron derivative functional groups into —BX$_3^-$ anionic groups, wherein X is independently selected from the group consisting of F, alkoxy and OH; and wherein general formula V is:

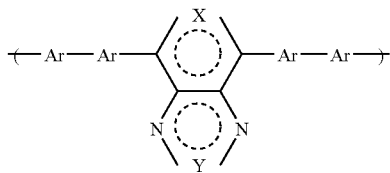

where X' is O, S, NR$_5$, R$_5$C—CR$_6$ or R$_5$C=CR$_6$; Y is O, S, NR$_7$, R$_7$C—CR$_8$ or R$_7$C=CR$_8$; R$_5$, R$_6$, R$_7$ and R$_8$ are the same or different and each is independently H or a substituent group; and each Ar is the same or different and is independently a substituted or unsubstituted aryl or heteroaryl group.

26. A method for making a polymer which includes the step polymerizing in a reaction mixture:
   (a) a first aromatic monomer comprising a first repeat unit as defined in general formula V and one reactive halide functional group and one reactive boron derivative group selected from a boronic acid group, a boronic ester group and a borane group; and
   (b) a second aromatic monomer comprising further of the first repeat unit and/or a second repeat unit Ar$_1$ that is a substituted or unsubstituted aryl or heteroaryl group, and one reactive halide functional group and one reactive boron derivative group selected from a boronic acid group, a boronic ester group and a borane group,
   wherein the reaction mixture comprises a catalytic amount of a catalyst suitable for catalyzing the polymerization of the aromatic monomers, and an organic base in an amount sufficient to convert the reactive boron derivative functional groups into —BX$_3^-$ anionic groups, wherein X is independently selected from the group consisting of F, alkoxy and OH; and where general formula V is:

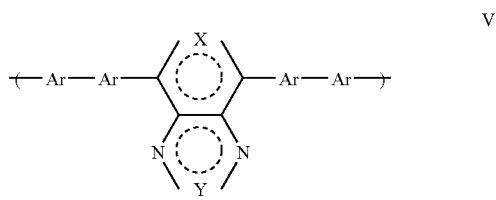

where X' is O, S, NR$_5$, R$_5$C—CR$_6$ or R$_5$C=CR$_6$; Y is O, S, NR$_7$, R$_7$C—CR$_8$ or R$_7$C=CR$_8$; R$_5$, R$_6$, R$_7$ and R$_8$ are the same or different and each is independently H or a substituent group; and each Ar is the same or different and is independently a substituted or unsubstituted aryl or heteroaryl group.

27. A method according to claim 25, wherein each Ar independently is substituted or unsubstituted and is selected from the group consisting of phenylene, thiophene, furan, pyridine, pyrrole, quinoxaline, benzothiadiazole, benzofuranodiazole, benzotriazole, other diazines and 1,3,5 triazines.

28. A method according to claim 27, having general formula II:

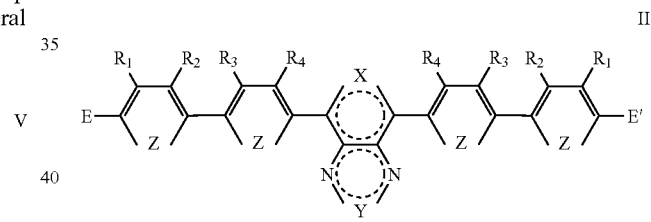

where E, E', X, Y, R5, R6, R7 and R8 are as defined in claim 1 and each Z is the same or different and is independently O, S, NR or RC=CR and R, R$_1$, R$_2$, R$_3$ and R$_4$ are the same or different and each is independently H or a substituent group.

29. A method according to claim 28, having general formula III:

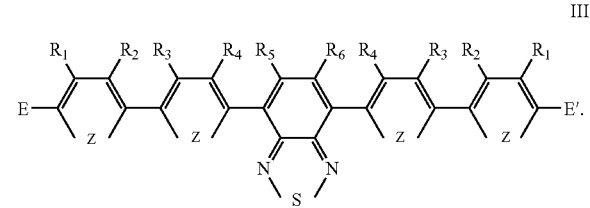

30. A method according to claim 28, where each Z is the same or different and is independently S or O.

31. A method according to claim 25, where at least one Ar comprises at least one C$_{1-10}$ alkyl or C$_{1-10}$ alkoxy substituent group.

32. Method of claim 25, wherein the polymer comprises a first repeat unit comprising a unit having general formula V that is substituted or unsubstituted:

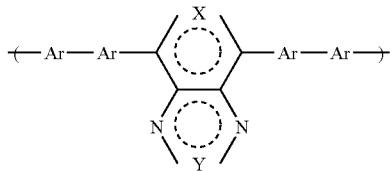

V where X is O, S, NR$_5$, R$_5$C—CR$_6$ or R$_5$C=CR$_6$; Y is O, S, NR$_7$, R$_7$C—CR$_8$ or R$_7$C=CR$_8$; R$_5$, R$_6$, R$_7$ and R$_8$ are the same or different and each is independently H or a substituent group; and each Ar is the same or different and is independently a substituted or unsubstituted aryl or heteroaryl group, and provided that none of the Ar groups comprise a mono fluorene group.

33. A method according to claim 32, wherein each Ar is the same or different and each independently is a substituted or unsubstituted heteroaryl group.

34. Optical device including a component comprising a polymer comprising a first repeat unit comprising a unit having general formula V that is substituted or unsubstituted:

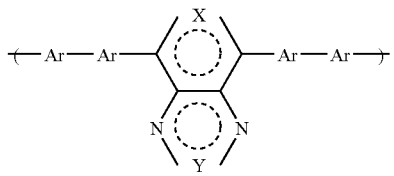

V where X is O, S, NR$_5$, R$_5$C—CR$_6$ or R$_5$C=CR$_6$; Y is O, S, NR$_7$, R$_7$C—CR$_8$ or R$_7$C=CR$_8$; R$_5$, R$_6$, R$_7$ and R$_8$ are the same or different and each is independently H or a substituent group; and each Ar is the same or different and is independently a substituted or unsubstituted aryl or heteroaryl group, and provided that none of the Ar groups comprises a mono fluorene group.

35. An optical device or a component therefor, which comprises a substrate and a polymer supported on the substrate, the polymer comprising a first repeat unit comprising a unit having general formula V that is substituted or unsubstituted:

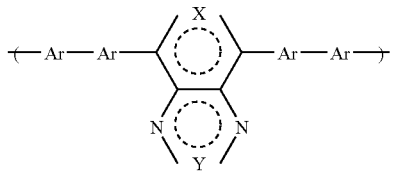

V where X is O, S, NR$_5$, R$_5$C—CR$_6$ or R$_5$C=CR$_6$; Y is O, S, NR$_7$, R$_7$C—CR$_8$ or R$_7$C=CR$_8$; R$_5$, R$_6$, R$_7$ and R$_8$ are the same or different and each is independently H or a substituent group; and each Ar is the same or different and is independently a substituted or unsubstituted aryl or heteroaryl group, and provided that none of the Ar groups comprises a mono fluorene group.

36. An optical device according to claim 35, wherein the optical device comprises an electroluminescent device.

37. An optical device according to claim 36, wherein the electroluminescent device comprises:

a first charge injecting layer for injecting positive charge carriers;

a second charge injecting layer for injecting negative charge carriers;

a light-emissive layer located between the first and second charge injecting layers comprising a light-emissive material for accepting and combining positive and negative charge carriers to generate light:

wherein the light-emissive material comprises said polymer.

38. A method for making a polymer comprising reacting a first aromatic monomer having general formula I, which may be substituted or unsubstituted, with a second aromatic monomer, which may be the same or different from the first aromatic monomer, under conditions suitable for polymerizing the monomers:

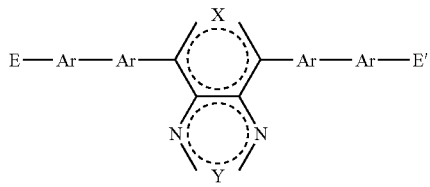

I wherein E and E' are the same or different and are reactive groups capable of undergoing chain extension; X is O, S, NR$_5$, R$_5$C—CR$_6$ or R$_5$C=CR$_6$; Y is O, S, NR$_7$, R$_7$C—CR$_8$ or R$_7$C=CR$_8$; R$_5$, R$_6$, R$_7$ and R$_8$ are the same or different and each is independently H or a substituent group; and each Ar is the same or different and is independently a substituted or unsubstituted aryl or heteroaryl group.

* * * * *

UNITED STATES PATENT AND TRADEMARK OFFICE
CERTIFICATE OF CORRECTION

PATENT NO. : 7,534,503 B2
APPLICATION NO. : 10/470049
DATED : May 19, 2009
INVENTOR(S) : Jeremy H. Burroughes et al.

It is certified that error appears in the above-identified patent and that said Letters Patent is hereby corrected as shown below:

On the Cover Page:
At field (57), line 4, "$R_5=CR_6$" should be -- $R_5C=CR_6$ --

Signed and Sealed this

Twenty-third Day of March, 2010

David J. Kappos
*Director of the United States Patent and Trademark Office*